(12) United States Patent
Gay et al.

(10) Patent No.: US 7,553,657 B2
(45) Date of Patent: *Jun. 30, 2009

(54) SUBSTRATES CONTAINING A TRICHODERMA ASPERELLUM STRAIN FOR BIOLOGICAL CONTROL OF FUSARIUM AND RHIZOCTONIA

(75) Inventors: Maria Isabel Trillas Gay, Barcelona (ES); Maria Lurdes Cotxarrera Vilaplana, Barcelona (ES)

(73) Assignee: Universidad de Barcelona, Barcelona (ES)

( * ) Notice: Subject to any disclaimer, the term of this patent is extended or adjusted under 35 U.S.C. 154(b) by 347 days.

This patent is subject to a terminal disclaimer.

(21) Appl. No.: 10/744,675

(22) Filed: Dec. 23, 2003

(65) Prior Publication Data

US 2004/0136964 A1 Jul. 15, 2004

Related U.S. Application Data

(63) Continuation of application No. PCT/ES02/00311, filed on Jun. 25, 2002.

(30) Foreign Application Priority Data

Jun. 26, 2001 (ES) ............................... 200101552

(51) Int. Cl.
*C12N 1/14* (2006.01)
*A01N 63/00* (2006.01)
*A01N 63/04* (2006.01)

(52) U.S. Cl. ................ 435/256.7; 435/254.6; 424/93.5; 424/93.1; 504/117

(58) Field of Classification Search ............... 435/256.7, 435/254.6; 424/93.5, 93.1; 504/117
See application file for complete search history.

(56) References Cited

U.S. PATENT DOCUMENTS 4,489,161 A * 12/1984 Papavizas ................. 435/256.7
4,748,021 A 5/1988 Chet et al.
4,900,348 A 2/1990 Hoitink

FOREIGN PATENT DOCUMENTS

WO WO 00/44222 8/2000
WO WO 01/84935 11/2001

OTHER PUBLICATIONS

Lieckfeldt et al. A morphological and molecular perspective of Trichoderma viride: is it one or two species? Appl Environ Microbiol. Jun. 1999;65(6):2418-28.*
Chef, D.G., et al., "Effects of Organic Components in Container Media on Suppresion of Fusarium Wilt of Chrysanthemum and Flax", *Disease Control and Pest Management*, vol. 73, No. 2, (1983), 279-81.
Cotxarrera, L. , et al., "Use of sewage sludge compost and Trichoderma asperellum isolates to suppress Fusarium wilt of tomato", *Soil Biology and Biochemistry 34*, (2002), 467-476.
Grondona, I. , et al., "Physiological and Biochemical Characterization of Trichoderma harzianum, a Biological Control Agent against Soilborne Fungal Plant Pathogens", *Applied and Environmental Microbiology*, (Aug. 1997), 3189-3198.
Hermosa, M. R., et al., "Molecular Characterization and Identification of Biocontrol Isolates of trichoderma spp.", *Applied and Environmental Microbiology*, (May 2000),1890-1898.
Hoitink, Haj , et al., "Biocontrol Within The Context Of Soil Microbial Communities: A Substrate-Dependent Phenomenon".
Larkin, Robert P., et al., "Efficacy of Various Fungal and Bacterial Biocontrol Organisms for Control of fusarium Wilt of Tomato", *Plant Disease*, vol. 82, No. 9, (1998),1022-1028.
Lieckfeldt, Elke , et al., "A Morphological and Molecular Perspective of Trichoderma viride: Is It One or Two Species?", *Applied and Environmental Microbiology*, (Jun. 1999),2418-2428.

* cited by examiner

*Primary Examiner*—L Blaine Lankford
*Assistant Examiner*—Taeyoon Kim
(74) *Attorney, Agent, or Firm*—Schwegman, Lundberg & Woessner, P.A.

(57) ABSTRACT

The strain of *Trichoderma asperellum* T34(2) CECT No. 20417 is useful for preparing substrates for biological control of vascular fusariose and death of plants caused by *Rhizoctonia solani*. The substrates can be peats, composts (hardwood compost, pine bark compost, cork compost, sludge compost from sewage treatment plants, garden residues, etc.) or formulations based on CPV-type compost (compost+peat+vermiculite). The fact that the substrates suppress both *Fusarium oxysporum* f. sp. *lycopersici* and *Rhizoctonia solani* provides an advantage in comparison with other substrates known in prior art. Another advantage is that the use of methyl bromide, a highly harmful product for the environment, in the control of vascular fusariose is avoided.

15 Claims, 3 Drawing Sheets

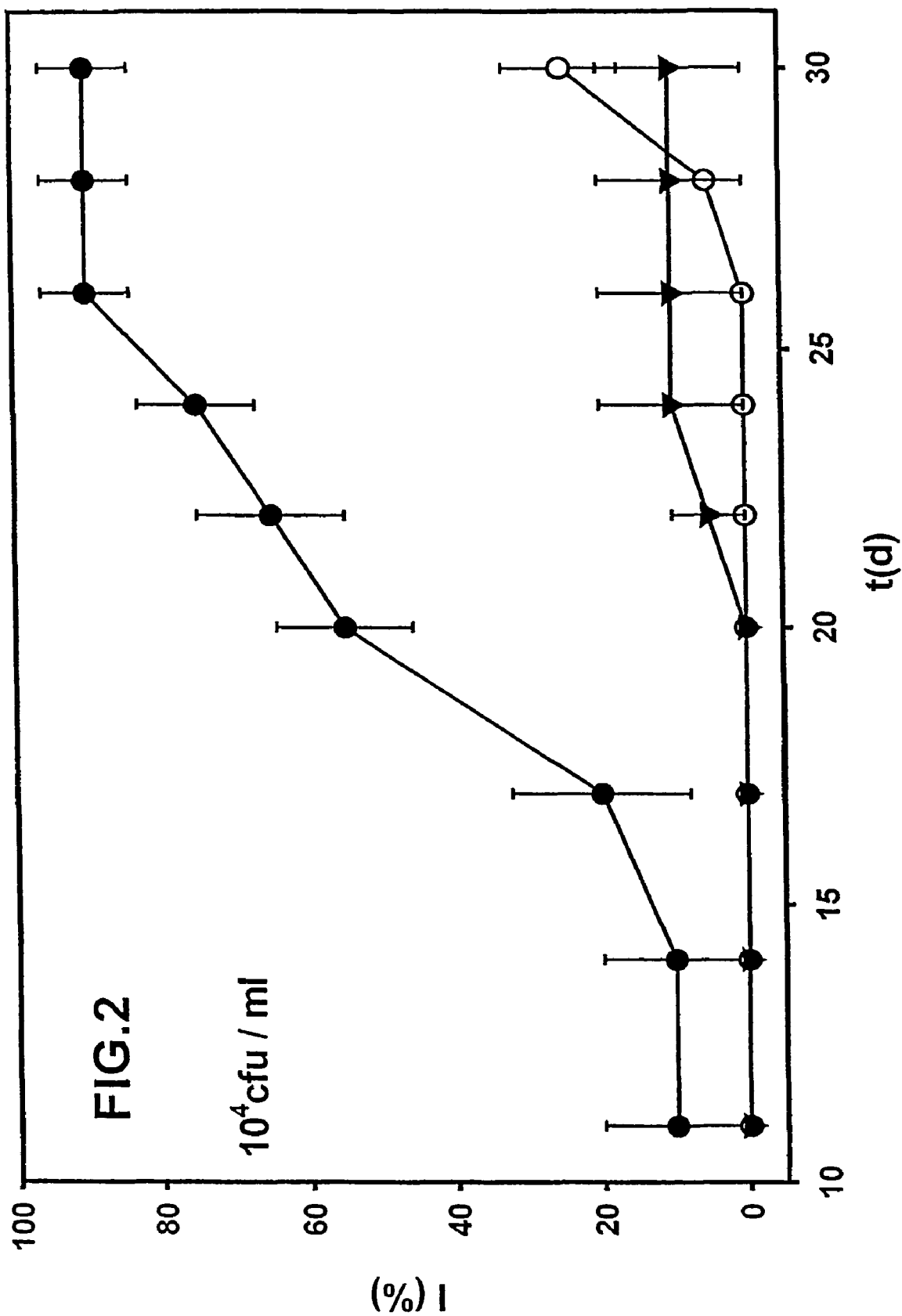

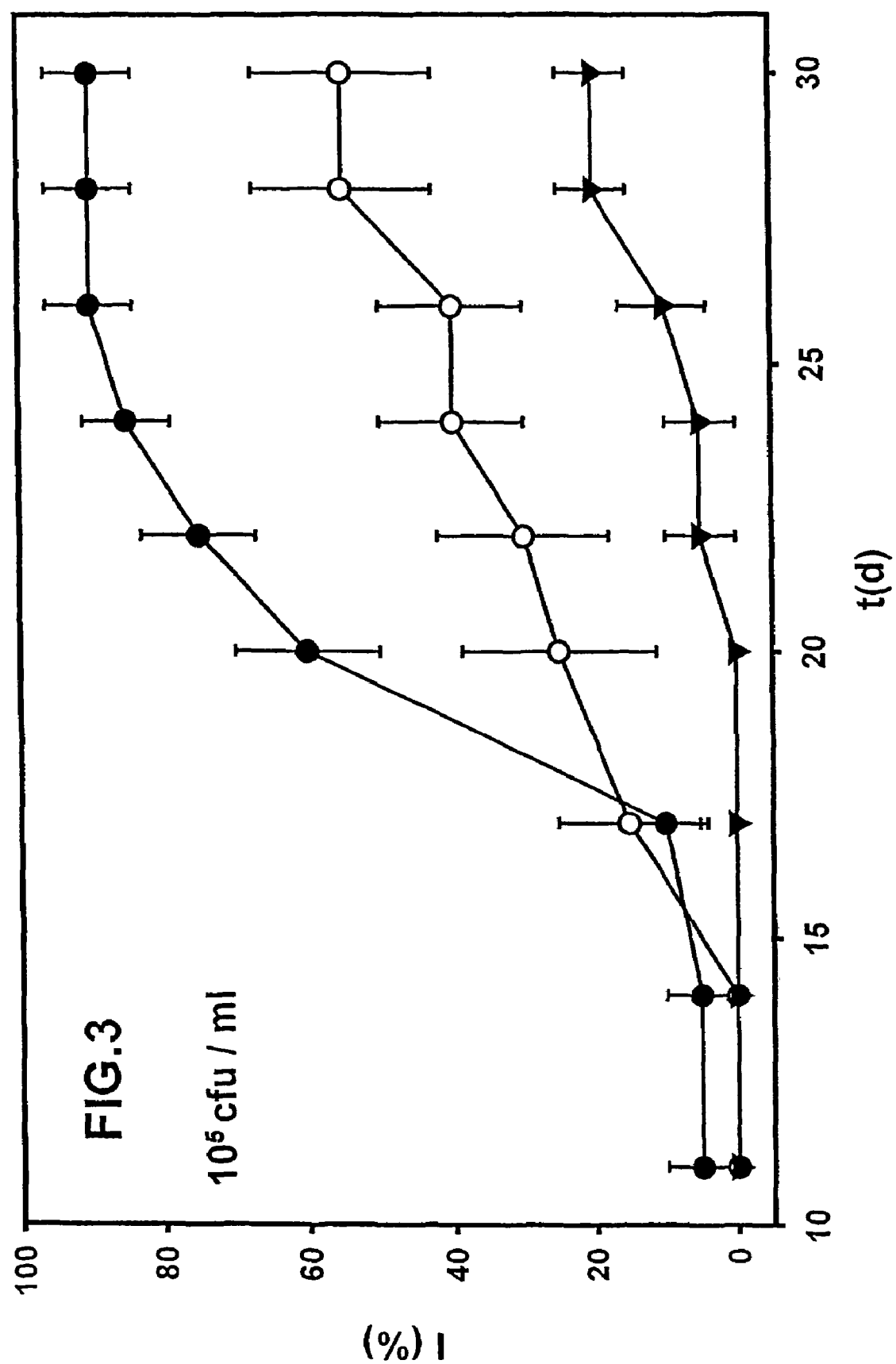

SUBSTRATES CONTAINING A TRICHODERMA ASPERELLUM STRAIN FOR BIOLOGICAL CONTROL OF FUSARIUM AND RHIZOCTONIA

This application is a continuation under 35 U.S.C. 111(a) of International Patent Application No. PCT/ES02/00311, filed on Jun. 25, 2002, which claims priority from Spanish Application Serial No. P 0101552, filed on Jun. 26, 2001, both of which applications are incorporated by reference in their entirety.

This invention refers to suppressive container media (e.g. composts or peats) for disease suppression or plant growth, in which one microorganism antagonistic to plant pathogens is added to the container media.

BACKGROUND ART

A container medium is a mix of a diversity of materials that can be used for growing plants. A container medium (also named substrate, potting mix, plant growing media, potting soil, etc.) generally comprises one or more light weight neutral aggregates (silica sand, perlite, vermiculite, expanded polystyrene, etc.), and an organic constituent (Sphagnum peat, composts, etc.), optionally with soil. The amounts included of the aforementioned ingredients vary widely among various container media, depending on the container size, the irrigation system and their ultimate utilization.

Composts prepared from heterogeneous wastes and used in container media may be naturally suppressive against a variety of diseases caused by soil-borne plant pathogens, or may become so upon the addition of antagonistic microorganisms. This suppressive effect can be highly variable. Compost and compost-amended media are usually more suppressive than Sphagnum peat-media because of the populations and activities of the microbial communities that are able to sustain. Composts can provide energy source for a great diversity of microorganisms and facilitate the biological control of plant pathogens. However, when Sphagnum peat is used as a sole organic component in a plant growth media, this media is a poor energy source and usually do not suppress plant diseases.

Two frequent diseases of plants are wilts and damping-off caused by some fungi (*Fusarium oxysporum, Verticillium* spp., *Rhizoctonia solani*). *Fusarium* wilts are diseases caused by several f. sp. (formae specialis, special forms) and races of *Fusarium oxysporum*. These wilts cause severe losses on many crops, specially in high temperature regions, and they are difficult to be controlled by chemicals (often the highly contaminant methyl bromide has to be used). Rhizoctonia damping-off is one of the most serious diseases of nursery crops throughout the world. Some specific antagonistic microorganisms, especially members of the genera *Pseudomonas* and *Trichoderma*, have been used to suppress the above-mentioned diseases. However, in practice it has proved to be very difficult to ensure that these antagonistic microorganisms in the plant growing media do achieve sufficient population densities to effectively suppress the plant disease. Consequently, in order to render a suppressive plant growth media for agricultural purposes, there is a need for new methods to produce or ensure sufficient populations of desired microorganisms. In this sense, artificial inoculation of container media formulated preferably with compost and antagonistic microorganisms is more suitable. Finally, in view of the significant losses caused to various commercial crops by *Fusarium oxysporum* and *Rhizoctonia solani*, it is highly desirable a method of reproducibly producing container media which is suppressive to both pathogens.

Some attempts to biologically control plant diseases are known where *Trichoderma* spp. are used. Thus, for instance, U.S. Pat. No. 4,900,348 discloses a method for producing a container medium which is suppressive to diseases caused by *Rhizcotonia solani* and *Pythium ultimum* which employs a mixture of *Trichoderma hamatum* isolate 382 and *Flavobacterium balustinum* isolate 299. U.S. Pat. No. 4,642,131 discloses a method where *Trichoderma hamatum* is used in combination with bacteria. However, none of these methods allows the control of *Fusarium* wilts what is an important limitation, given that in practice these wilts have to be mainly controlled by using methyl bromide, a highly hazardous chemical which causes serious environmental problems.

SUMMARY OF THE INVENTION

According to an aspect of the present invention, there is provided a biologically pure culture of fungus *Trichoderma asperellum* isolate T34(2) for inducing suppression of plant diseases caused by *Rhizoctonia solani* and/or *Fusarium oxysporum* f. sp. *lycopersici*. *Trichoderma asperellum* isolate 34(2) was deposited on Mar. 28, 2001, in the Spanish Collection of Type Cultures (Colección Española de Cultivos Tipo, Universidad de Valencia, 46100 Burjassot, Valencia, Spain) with CECT No. 20417, according to the Budapest Treaty on the International Recognition of the Deposit of Microorganisms for the Purposes of Patent Procedure.

The antagonistic *Trichoderma asperellum* isolate T34(2) was isolated from a suppressive compost-amended plant growing medium (CPV; compost: peat: vermiculite; 2:1:1 v/v) prepared from the organic fraction of pre-consumer food, sewage sludge and yard wastes. Cork compost (CC), Sphagnum peat (P) and CPV were inoculated with a conidial suspension of a pure culture of this isolate, and tested for its ability to suppress *Fusarium* wilt and Rhizoctonia damping-off. Natural cork compost and heat-treated Sphagnum peat inoculated with *Trichoderma asperellum* isolate T34(2) suppress Rhizoctonia damping-off of cucumber. Sterilized CPV media inoculated with *Trichoderma asperellum* isolate T34 (2) suppress *Fusarium* wilt of tomato.

Another aspect of the present invention relates to a method for producing a container medium suppressive to *Fusarium oxysporum* f. sp. *lycopersici*, *Rhizoctonia solani* or diseases caused thereby, which comprises inoculating into the container medium the *Trichoderma asperellum* isolate T34(2) CECT No. 20417.

The materials used to produce suppressive container media according to the method of the present invention can be selected among those commonly used in the art. In particular embodiments container media are peats, such as Sphagnum peat. In other embodiments, container media are composts, being particularly preferred those made of composted hardwood bark, pine bark, cork, sewage sludge and/or yard wastes. Particularly preferred as container media are the compost-amended plant growing media of the CPV (compost+peat+vermiculite) type.

Another aspect of the invention refers to the use of *Trichoderma asperellum* isolate T34(2), as a biological control agent against the *Fusarium* wilt. In comparison with the current use of methyl bromide for the treatment of this wilt, the present invention has the advantage of being environmentally less harmful.

Another aspect of the invention relates to the use of the *Trichoderma asperellum* isolate T34(2) as a biological control agent against Rhizoctonia damping-off, a problem of great economic importance.

An important advantage of the suppressive container media of the present invention compared to those known in the art, is that they are suppressive to both diseases, *Fusarium* wilt and Rhizoctonia damping-off, not only to one of them. This is advantageous from the point of view of simplicity and economy.

DESCRIPTION OF THE DRAWINGS

FIGS. 2 and 3 are charts of disease incidence (I), expressed as percentage (%), corresponding to *Fusarium* wilt progress with time (t, in days) for tomato plants variety "Roma" grown in CPV mix natural (open circles), sterilized (filled circles) or sterilized and inoculated with *Trichoderma asperellum* isolate T34(2) (triangles). Container media were infested with *Fusarium oxysporum* f. sp. *lycopersici* race 1 at $10^4$ (in FIG. 2) or $10^5$ (in FIG. 3) colony forming units (cfu) per milliliter of substrate. Disease incidence ranked from 0% (all plants asymptomatic) to 100% (all plants symptomatic). Every curve represents the average of at least five pots, each containing four plants.

DETAILED DESCRIPTION OF THE INVENTION

Figure 1:
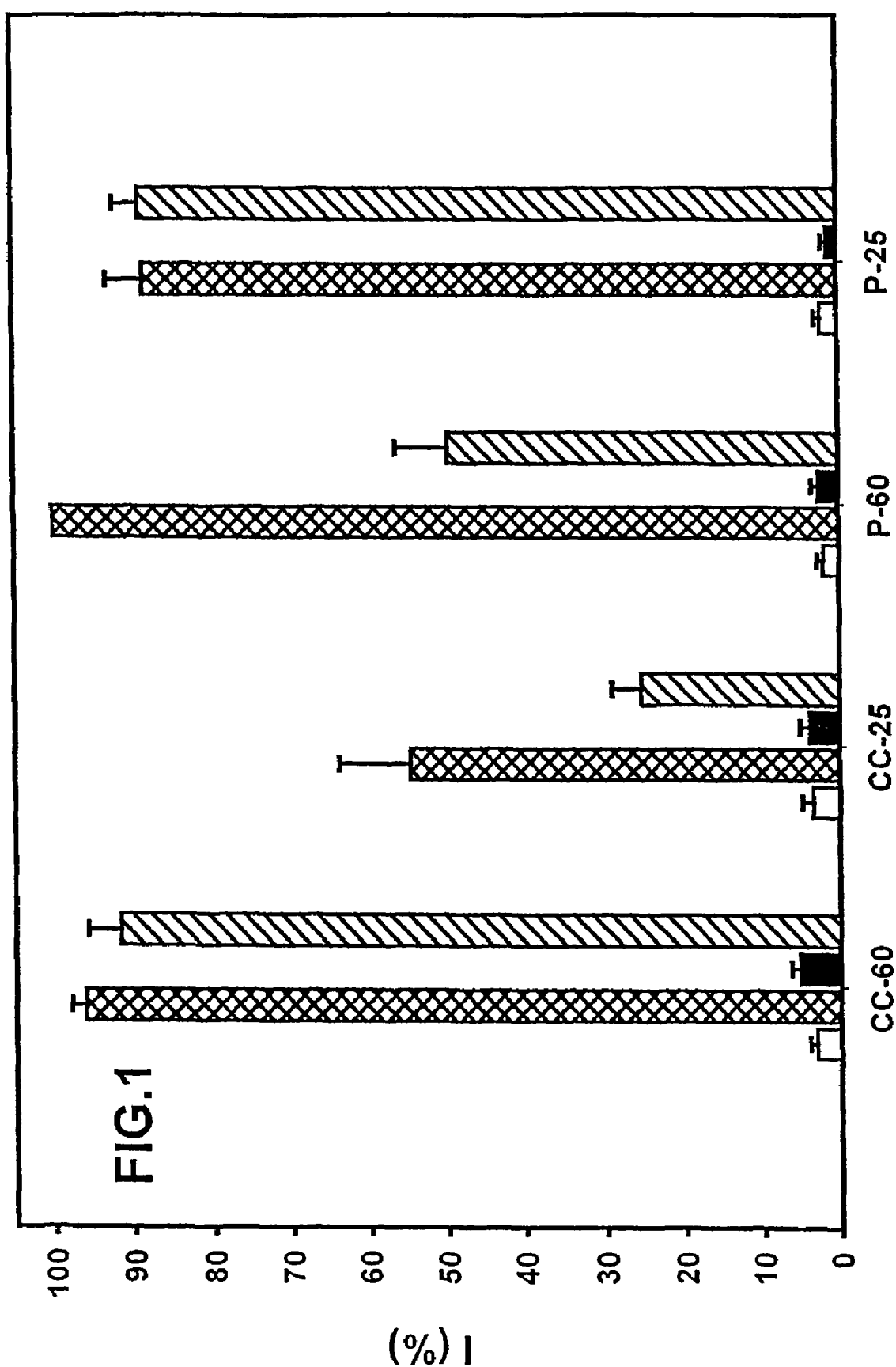
FIG. 1 is a chart bar of the disease incidence (I), expressed as percentage (%), corresponding to Rhizoctonia damping-off in cucumber seedling variety "Negrito", grown in composted cork (CC) or Sphagnum peat (P), either heat-treated at 60° C. (CC-60 and P-60) or non-treated (at 25° C.: CC-25, P-25), and inoculated or non-inoculated with the antagonistic *Trichoderma asperellum* isolate T34(2). The control treatments show the results for the container media non inoculated with the pathogen (open bar: container medium non inoculated with T34(2); filled bar: container medium inoculated with T34(2)). The inoculated treatments show the results for the container media inoculated with the pathogen (squares pattern: container medium non inoculated with T34(2); lines pattern: container medium inoculated with T34(2)). Disease incidence ranked from 0% (all plants asymptomatic) to 100% (all plants symptomatic). Every bar represents the average of fifteen pots, each containing fifteen plants. Every experiment was repeated at least three times.

1. Isolation and Characterization of the *Trichoderma asperellum* Isolate

The method used for the isolation of *Trichoderma* spp. was serial dilution plating on a modified Potato-Dextrose-Agar (PDA plus. chlortetracycline, 50 mg/l, and tergitol NP-10, 1 ml/l). Colonies of *Trichoderma* spp. were identified by stereomicroscopy using the keys of Rifai (cf. M. A. Rifai, "A revision of the genus *Trichoderma*. Commonwealth Mycological Institute", *Mycological papers* 1969, no. 116, pp. 1-56), and single spore cultures of the isolates were obtained. The identification of the isolate T34(2) as *Trichoderma asperellum* was performed by sequencing the internal transcribed spacer 1 (ITS1), adjacent to 5.8S rRNA gene (M. R. Hermosa et al., "Molecular characterization and identification of biocontrol isolates of *Trichoderma* spp.", *Applied and Environmental Microbiology* 2000, vol. 66, pp. 1890-1898). The ITS1 sequence accession number for this isolate is AJ278564 (EMBL Nucleotide Sequence Database).

2. Bioassay to Evaluate the Ability to Suppress Rhizoctonia Damping-Off

The isolate AC-4 of *Rhizoctonia solani* originally isolated from melon (provided by Dr. Tello, Universidad Almeria) was grown in Potato-Dextrose-Agar (PDA). An inoculum of this pathogen was obtained in air-dried chopped potato/soil mixture (pieces of 1.0 mm) as described (E. B. Nelson et al., "Factors affecting suppression of *Rhizoctonia solani* in container media", *Phytopathology* 1982, vol. 72, pp. 275-279). To assess the ability of T34(2) to suppress Rhizoctonia damping-off, composted cork (CC) and Sphagnum peat (P), either natural or heat-treated (60° C., 6 days) were inoculated with a conidial suspension of T34(2) at a final concentration of 1000 cfu/ml container medium. The inoculated media were incubated at room temperature for fifteen days to achieve the colonization of the media by the biocontrol agent. Composted cork (CC) and Sphagnum peat (P) non-inoculated with T34 (2) were introduced as positive controls. After incubation, *Rhizoctonia solani* chopped potato/soil inoculum was added to the media at the rate of 1.5 g per 2 l of container medium. Composted cork (CC) and Sphagnum peat (P) non-infested with *Rhizoctonia solani* were introduced as negative controls. Container media were distributed into pots (9-cm-pots, 330 ml volume, five pots per treatment). Cucumbers seeds var. "Negrito" were planted at a ratio of fifteen per pot and covered with 1.0 cm container medium. Pots were distributed randomly in a growth chamber ($25\pm2°$ C., 16 h light and 150-210 $\mu$mol/m$^2$s photosynthetic active radiation intensity), irrigated with a complete nutrient solution and submitted to a 7-day-bioassay. Disease incidence measured as the percentage of symptomatic plants was evaluated per each pot at the end of the bioassay. All experiments were performed at least three times.

FIG. 1 shows the results obtained with the composted cork (CC) and Sphagnum peat (P). The natural composted cork is a moderate suppressive media to Rhizoctonia damping-off (disease incidence 55%) compared with the natural peat (disease incidence 88%). The heat-treatment of both composted cork (CC) and Sphagnum peat (P) caused the complete lost of suppressiveness of the media. The *Trichoderma asperellum* T34(2) isolate consistently increased ($P \leq 0.05$) the ability of the natural composted cork (CC) and the heat-treated Sphagnum peat (P) to suppress Rhizoctonia damping-off of cucumber. When the natural composted cork (CC) was inoculated with T34(2) disease incidence decreased 30% compared to the natural CC non inoculated with T34(2). When the heat-treated peat (P) was inoculated with T34(2) disease incidence decreased 50% compared to the non-inoculated peat (P). Results presented in this graph demonstrate that T34(2) can be effective to control Rhizoctonia damping-off when inoculated into the appropriate potting medium.

3. Bioassay to Evaluate the Ability to Suppress *Fusarium* Wilt

The isolate RAF 70 of *Fusarium oxysporum* f. sp. *lycopersici* race 1 (FOL), obtained from Universidad de Almeria, through Dr. Tello, was grown in malt extract broth for 5 days at 25° C. on a rotary shaker. Conidia were recovered from this liquid culture by centrifugation (6000 g, 20 min), rinsed twice and resuspended with sterile distilled water. The conidial suspension was mixed with sterile talc (⅓ conidial suspension, ⅔ talc v/w), dried under sterile conditions in a laminar flow cabinet, sieved (200 μm) and stored at 4° C. The inoculum concentration of talc was finally determined by the serial dilution technique on Potato Dextrose Agar (PDA, Sigma-Aldrich).

Compost prepared from the organic fraction of pre-consumer food, sewage sludge and yard wastes was mixed with Sphagnum peat and vermiculite in a 2:1:1 ratio (v/v) to obtain a compost-amended mix (CPV). This mix was either stored at room temperature (natural CPV), sterilized (1 h, 120° C.) three consecutive days (sterilized CPV) or sterilized and post-inoculated with a conidial suspension of T34(2) at a final concentration of 1000 colony forming units for cubic centimeter of mix. The sterilized mix inoculated with T34(2) was incubated fifteen days to achieve the colonization of the sterilized mix by the biocontrol agent. The container media were infested with the talc inoculum of FOL at $10^4$ or $10^5$ cfu/ml container medium, and distributed into pots (9-cm-pots, 330 ml volume, five pots per treatment). Container media non-infested with the pathogen were introduced as negative controls. Four plantlets of tomato variety "Roma" were planted in each pot. Pots were then placed in a growth chamber ($25\pm2°$ C., 16 h light and 150-210 $\mu mol/m^2 s$ photosynthetic active radiation intensity) and irrigated with a complete nutrient solution. Disease incidence measured as the percentage of symptomatic plants was evaluated from the appearance of first *Fusarium* wilt symptoms.

FIGS. 2 and 3 show the results obtained with the compost-amended potting mix. Sterilized CPV inoculated with the *Trichoderma asperellum* T34(2) isolate was highly suppressive to *Fusarium* wilt of tomato. Pathogen concentrations of $10^4$ and $10^5$ cfu/ml in this mix only caused a disease incidence of 10% (FIG. 2) and 12% (FIG. 3), whereas in the natural mix the equivalent pathogen concentrations caused disease incidences of 20% and 55% respectively, after 30 days of bioassay. In the sterilized mix non-inoculated with T34(2) the disease incidence reached 90% for both the pathogen concentrations assayed. In summary, results presented in these graphs show that T34(2) inoculated on the sterilized sewage-sludge-compost-amended medium significantly increase the ability of this medium to suppress *Fusarium* wilt (at $10^5$ cfu/ml) compared to the non-inoculated T34(2) media.

INCORPORATION BY REFERENCE

All publications, patents, and patent documents, cited in this application, are incorporated by reference herein, as though individually incorporated by reference. In the case of any inconsistencies, the present disclosure, including any definitions therein will prevail.

The invention claimed is:

1. A biologically pure culture for inducing suppression of plant pathogens and/or diseases caused by *Rhizoctonia solani* and/or *Fusarium oxysporum* f. sp. *lycopersici* in a container medium, said culture comprising a *Trichoderma asperellum* isolate T34 (2) CECT No. 20417.

2. A method for producing a container medium suppressive to *Fusarium oxysporum* f. sp. *lycopersici* and/or *Rhizoctonia solani* and/or diseases caused thereby, which method comprises inoculating *Trichoderma asperellum* isolate T34 (2) CECT No. 20417 into said container medium.

3. A method according to claim 2 wherein the container medium comprises a peat.

4. A method according to claim 2 wherein the container medium comprises a compost.

5. A method according to claim 4 wherein the compost is composted hardwood bark.

6. A method according to claim 4 wherein the compost is composted pine bark.

7. A method according to claim 4 wherein the compost is composted cork.

8. A method according to claim 4 wherein the compost is composted sewage sludge.

9. A method according to claim 4 wherein the compost is composted yard wastes.

10. A method according to claim 2 wherein the container medium comprises a compost-amended plant growing medium of the CPV (compost-peat-vermiculite) type.

11. A method to suppress *Fusarium* wilt comprising growing plants threatened by *Fusarium* wilt in a container medium comprising *Trichoderma asperellum* isolate T34 (2) CECT No. 20417 in an amount effective to suppress *Fusarium* wilt.

12. A method to suppress *Rhizoctonia* damping-off comprising growing plants threatened by *Rhizoctonia* damping-off in a container medium comprising *Trichoderma asperellum* isolate T34 (2) CECT No. 20417 in an amount effective to suppress *Rhizoctonia* damping-off.

13. A biologically pure culture of *Trichoderma asperellum* isolate T34(2) CECT No. 20417.

14. A biologically pure culture for inducing suppression of plant pathogens and/or diseases caused by *Rhizoctonia solani* and *Fusarium oxysporum* f. sp. *lycopersici* in a container medium, said culture comprising a *Trichoderma asperellum* isolate T34 (2) CECT No. 20417.

15. A biologically pure culture for inducing suppression of plant pathogens and/or diseases caused by *Rhizoctonia solani* in a container medium, said culture comprising a *Trichoderma asperellum* isolate T34 (2) CECT No. 20417.

* * * * *